United States Patent
Ein-Gal

(10) Patent No.: US 11,883,047 B2
(45) Date of Patent: Jan. 30, 2024

(54) ELECTROMAGNETIC SHOCKWAVE TRANSDUCER

(71) Applicant: Moshe Ein-Gal, Ramat Hasharon (IL)

(72) Inventor: Moshe Ein-Gal, Ramat Hasharon (IL)

( * ) Notice: Subject to any disclaimer, the term of this patent is extended or adjusted under 35 U.S.C. 154(b) by 1058 days.

(21) Appl. No.: 16/558,195

(22) Filed: Sep. 2, 2019

(65) Prior Publication Data

US 2021/0059699 A1    Mar. 4, 2021

(51) Int. Cl.
*A61B 17/225* (2006.01)
*G10K 9/12* (2006.01)

(52) U.S. Cl.
CPC ...... *A61B 17/2258* (2013.01); *A61B 17/2251* (2013.01); *G10K 9/12* (2013.01)

(58) Field of Classification Search
CPC .. A61B 17/2258; A61B 17/2251; G01K 9/12; G01N 29/036; G01N 33/52
See application file for complete search history.

(56) References Cited

U.S. PATENT DOCUMENTS

| | | | | |
|---|---|---|---|---|
| 5,165,388 A * | 11/1992 | Hartinger | .................. | H01F 6/06 367/175 |
| 5,214,620 A * | 5/1993 | Rattner | ..................... | G10K 9/12 367/175 |
| 5,230,328 A * | 7/1993 | Buchholtz | ................ | G10K 9/12 601/4 |
| 5,233,972 A * | 8/1993 | Rattner | ..................... | G10K 9/12 601/4 |
| 5,251,630 A * | 10/1993 | Rattner | ..................... | G10K 9/12 367/175 |
| 5,268,879 A * | 12/1993 | Flanagan | ............... | H04R 23/00 367/175 |
| 6,208,884 B1 * | 3/2001 | Kumar | ................... | G01R 33/16 324/207.21 |
| 6,719,449 B1 * | 4/2004 | Laugharn, Jr. | ...... | B01F 35/2115 366/127 |
| 6,799,465 B2 * | 10/2004 | Berman | .................. | G01M 7/08 73/590 |
| 8,298,162 B2 * | 10/2012 | Del Giglio | ....... | A61B 17/22012 601/3 |
| 2001/0029329 A1 * | 10/2001 | Avrin | ................... | A61B 5/4244 600/407 |
| 2006/0158956 A1 * | 7/2006 | Laugharn, Jr. | ......... | B01J 19/008 366/127 |
| 2007/0239081 A1 * | 10/2007 | Ein-Gal | ................ | G10K 11/30 601/4 |
| 2010/0056963 A1 * | 3/2010 | Shaviv | ............... | A61H 23/0218 604/385.01 |
| 2015/0231414 A1 * | 8/2015 | Ein-Gal | ................... | B06B 1/04 601/2 |
| 2018/0241116 A1 * | 8/2018 | Kerselaers | ........... | H04B 5/0031 |
| 2020/0326312 A1 * | 10/2020 | Sinha | ................... | G01N 29/028 |

* cited by examiner

*Primary Examiner* — Baisakhi Roy

(74) *Attorney, Agent, or Firm* — Dekel Patent Ltd.; David Klein

(57) ABSTRACT

An electromagnetic shockwave transducer includes a double-faced coil of wire wound around an insulator. The coil has a first coil face on one side of the insulator and a second coil face on an opposite side of the insulator. Coil ends of the coil are electrically coupled to a current source, which produces a current pulse in the coil so as to produce a force between the coil faces.

14 Claims, 1 Drawing Sheet

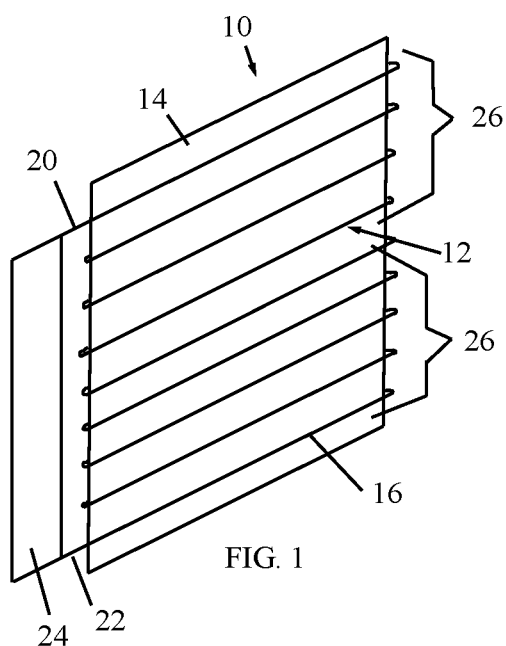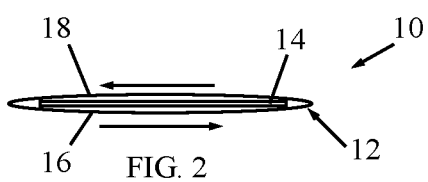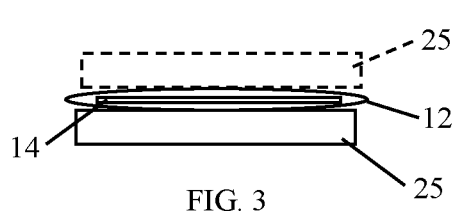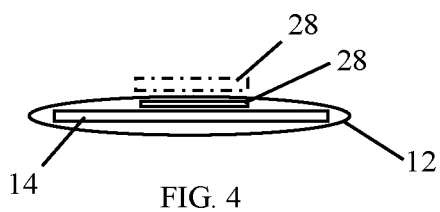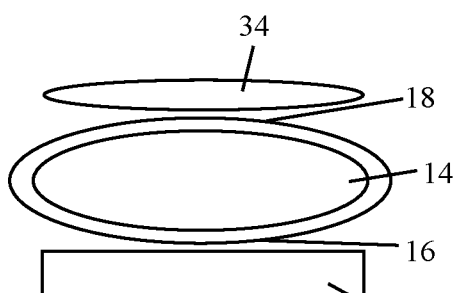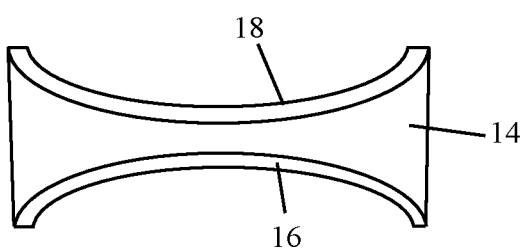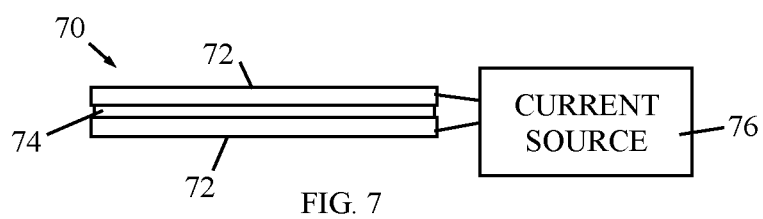

ELECTROMAGNETIC SHOCKWAVE TRANSDUCER

FIELD OF THE INVENTION

The present invention relates to a method and a system for shockwave generation and shockwave treatment, and particularly an electromagnetic shockwave transducer that includes two faces of one coil for generating pulsed compression shockwaves, and for an electromagnetic shockwaves transducer that includes two faces of two coils for generating pulsed rarefaction shockwaves, and for a combined system for sequentially producing rarefaction and compression pulsed acoustic waves.

BACKGROUND OF THE INVENTION

There are prior art electromagnetic shockwave transducers that include a surface flat coil attached to a backing material and a thin conductive membrane in close proximity to the coil. A current pulse applied to the surface coil induces eddy current in the thin conductive membrane. The membrane is then repelled and gives rise to acoustic waves in propagation medium, typically water, in contact with the membrane, directly or via a matching layer. Waves are also reflected from the backing material due to its high acoustic impedance. U.S. Pat. No. 4,928,672 is an example of such an electromagnetic transducer.

U.S. Pat. No. 7,443,764 to Clark et al. describes an electromagnetic transducer which does not involve inducing eddy currents in a membrane. Each of a pair of electrically conductive spiral coils is ensconced in a disk-shaped matrix. The two coil-ensconced matrices are joined face-to-face so as to sandwich between them a thin, non-magnetic elastic layer. Electrical current produced by a signal amplifier passes through each coil in opposing directions, creating opposing magnetic fields. Mechanical forces are generated directly by the opposing electrical currents in the two coils, and without the use of any magnetic core material. The inductance of the coil is coupled with a capacitor to produce a tunable LC (inductance-capacitance) electrical circuit. Elastic material is used between the coils to produce a tunable spring-mass system in which mechanical resonance is associated with the mass of the entrained water and the spring constant of the elastic material.

In short, U.S. Pat. No. 7,443,764 describes an oscillatory apparatus including two parallel spiral coils carrying currents in opposing directions, with an elastic separator between the coils intended to provide spring force so the device produces low frequency acoustic waves. A disadvantage of this arrangement is the limited electric field between the two coils since the voltage across a coil is in opposite polarity to the voltage across the other coil; the respective ends of the coils are subject to a voltage difference limited by related voltage breakdown. The limited voltage across the coil and/or a sufficiently large distance between the coils limits the repulsive force between the coils.

Another disadvantage is the non-uniformity of the produced force across the coil area due to the non-uniformity of the magnetic field strength of a flat coil and the linear relationship between the magnetic field strength and the produced force.

The mechanical and electrical resonances limit the operation of the acoustic oscillatory apparatus to low frequency waves, rendering the construction inadequate for producing shockwaves.

Prior art shockwave transducers are intended to produce compression waves. For applications requiring negative pressure waves (rarefaction), the tail of a compression shockwave pulse may be used. However, the tail pressure is significantly lower than the compression peak pressure.

SUMMARY OF THE INVENTION

The present invention seeks to provide novel electromagnetic shockwave transducers, as are described more in detail hereinbelow, which have use in many medical applications, such as but not limited to, lithotripsy, histotripsy, orthopedics, treating pathological tissue conditions, treating male impotence and many others, in particular, applications to soft tissue. The transducers are constructed to respectively produce pulsed rarefaction and compression acoustic waves (shockwaves).

The electromagnetic compression shockwave transducer of the invention includes one coil with two faces. The coil has windings made up of longitudinal winding segments; neighboring segments are spaced apart by a small distance. For example, the coil may be obtained by wounding a wire around a thin sheet (e.g., paper sheet) such that the winding segments are separated by the paper thickness and consequently the two faces of the coil, formed by corresponding windings segments, are respectively attached to the sheet faces (the two opposing faces or sides of the sheet).

The two coil faces are not subjected to high voltage between them; instead, as opposed to the prior art, the high voltage is applied between the coil ends and the interwinding voltage is limited by the number of windings. The separator (in the above example, the paper sheet) can therefore be very thin. In case the winding wire is adequately insulated, no separator may be needed. In addition, in contrast with the prior art, the separator does not have to be elastic, because the transducer of the invention produces shockwaves in pulses, not in oscillations. The invention thus produces greater and more uniform forces than the prior art two-coil configuration for similar parameters.

There is provided in accordance with a non-limiting embodiment of the invention an electromagnetic compression shockwave transducer including a double-faced coil of wire wound around an insulator, the coil having a first coil face on one side of the insulator and a second coil face on an opposite side of the insulator, wherein coil ends of the coil are electrically coupled to a current source, which produces a current pulse in the coil so as to produce a force between the coil faces.

The electromagnetic compression shockwave transducer may further include an acoustically conductive interface, adjacent one or both of the coil faces, and through which the force produces an acoustic wave. The acoustically conductive interface may be attached to one or both of the coil faces.

Current in the first coil face may generally flow in an opposite direction to current in the second coil face.

Each of the coil faces may include generally parallel coil segments.

In accordance with a non-limiting embodiment of the invention the double-faced coil includes two or more serially-connected sub-coils.

In accordance with a non-limiting embodiment of the invention a magnet is configured to produce a magnetic field generally perpendicular to coil segments of each the coil face.

The coil faces and/or the insulator may be generally planar or non-planar.

There is provided in accordance with a non-limiting embodiment of the invention an electromagnetic rarefaction shockwave transducer including two similarly shaped and parallel flat coils separated by a thin restoring insulator; the coils are in communication with a current source operable to deliver current pulses of same polarity to the coils so as to produce pulses of pulling forces between the coils. Coils position may be restored by restoring insulator following the current pulse.

There is provided in accordance with a non-limiting embodiment of the invention an electromagnetic shockwave bi-polar transducer including two similarly shaped flat coils separated by a thin insulator; the coils are in communication with a current source operable to sequentially deliver to the respective coils current pulses of same polarity and/or of opposite polarity so as to produce sequential pulses of pulling and/or pushing forces between the coils, so as to produce and transmit sequential pulses of rarefaction and compression acoustic waves to acoustic conductive interface.

BRIEF DESCRIPTION OF THE DRAWINGS

The present invention will be understood and appreciated more fully from the following detailed description taken in conjunction with the drawings in which:

FIG. 1 is a simplified pictorial illustration of an electromagnetic shockwave transducer, constructed and operative in accordance with an embodiment of the invention.

FIG. 2 is a simplified edge-view illustration of the electromagnetic shockwave transducer.

FIG. 3 is a simplified pictorial illustration of the electromagnetic shockwave transducer, in which one or both coil faces are attached to an acoustically conductive interface.

FIG. 4 is a simplified edge-view illustration of another variation of the electromagnetic shockwave transducer, in accordance with other embodiments of the invention, which includes a magnet.

FIGS. 5 and 6 are simplified edge-view illustrations of other variations of the electromagnetic shockwave transducer, in which the coil faces are generally non-planar.

FIG. 7 is a simplified illustration of an electromagnetic shockwave transducer for producing rarefaction shockwaves or a combination of compression and rarefaction shockwaves, in accordance with an embodiment of the invention.

DETAILED DESCRIPTION OF EMBODIMENTS

Reference is now made to FIGS. 1 and 2, which illustrate an electromagnetic shockwave transducer 10, constructed and operative in accordance with a non-limiting embodiment of the invention.

Transducer 10 includes a coil 12 of wire wound around an insulator 14, such that the coil 12 is double-faced, that is, the coil 12 has two faces 16 and 18 on opposite sides of insulator 14. Accordingly, coil 12 is a conductive coil that includes two coil faces 16 and 18 in close proximity. Each coil face 16 and 18 is made of generally parallel coil segments (although optionally, they may be non-parallel). Two coil ends 20 and 22 are electrically coupled to a current source 24, which produces a current pulse in the coil 12 so as to produce a force (Lenz force) between the coil faces 16 and 18.

In the illustrated embodiment of FIGS. 1 and 2, the insulator 14 is a thin flat insulator, made of an electrically insulating material, which may be soft or hard, flexible or stiff. Current in the respective coil faces 16 and 18 flows in opposite directions as indicated by the arrows in FIG. 2. As mentioned above, if the winding wire of coil 12 is adequately insulated, then no additional insulator 14 may be needed; the wire insulation acts as the insulator.

Reference is now made to FIG. 3. An acoustically conductive interface 25 is adjacent one or both coil faces, for example, for interfacing with patient tissue. The one or both coil faces may be attached to the acoustically conductive interface 25. The acoustically conductive interface 25 is preferably made of an electrically safe and bio-compatible material that exhibits mechanically efficient matching of respective acoustic impedances of the patient tissue and the bio-compatible material. Preferably, the bio-compatible material of transducer interface 25 has an acoustic impedance not lower than that of the patient tissue and not higher than that of the coil 12, and most preferably close (within 20%) to the geometric mean of the two.

The acoustic impedance (Z) of a material is defined as the product of its density ($\varphi$ and acoustic velocity (V), that is, $Z=\rho*V$, and is measured in Rayls (kg/(sec·m$^2$)] or more conveniently in MegaRayls (MRayls).

Reference is now made again to FIG. 1. In another version of the electromagnetic shockwave transducer, the double-faced coil may be configured as two or more serially-connected (e.g., flat) sub-coils 26 facing each other. (In other words, not one coil but two or more separate coils wound on the insulator.) Positioning of the coil faces of the sub-coils 26 determines whether current flows in the same direction in the respective faces or in the opposite direction, leading to the faces attracting or repelling each other, respectively.

Reference is now made to FIG. 4, which illustrates another version of the transducer 10 including a double-faced coil 12 and further including a magnet 28, which may be made of any suitable magnetic material, such as but not limited to, rare-earth materials, e.g., neodymium iron boron or samarium cobalt and the like, or non-rare-earth materials, e.g., different ferrous alloys. Magnet 28 may be a permanent magnet or an electromagnet and the like. Magnet 28 produces a magnetic field generally perpendicular to coil segments of each coil face. Magnet 28 may be internal to the coil 12 or external to the coil 12 (as shown in broken lines).

In the above embodiments, the coil faces are generally planar. Reference is now made to FIGS. 5 and 6, which illustrate other versions of the transducer in which the coil faces 16, 18 and/or the insulator 14 are generally non-planar, such as convex (FIG. 5) or concave (FIG. 6).

As another option, applicable for any of the embodiments described herein, as seen in FIG. 5, an acoustic lens 34 and/or an acoustic reflector 36 may be used with the transducer.

Reference is now made to FIG. 7, which illustrates an electromagnetic shockwave transducer 70 for producing rarefaction shockwaves or a combination of compression and rarefaction shockwaves, in accordance with an embodiment of the invention.

The electromagnetic rarefaction shockwave transducer 70 includes two similarly shaped and parallel flat coils 72 separated by a thin restoring insulator 74. The coils 72 are in electrical communication with a current source 76 operable to deliver current pulses of same polarity to the coils 72 so as to produce pulses of pulling forces that pull the coils 72 towards each other. The positions of the coils 72 may be restored by the restoring insulator 74 which eliminates any electromagnetic force after the current pulse is over. Each coil may include two or more sub-coils.

As similarly described for the embodiment of FIG. 3, the electromagnetic rarefaction shockwave transducer 70 may further include an acoustically conductive interface 25, adjacent one or both of the coil faces, and through which the force produces an acoustic rarefaction wave. The acoustically conductive interface may be attached to one or both of the coil faces.

As another option, as similarly described above with reference to FIG. 5, an acoustic lens 34 and/or an acoustic reflector 36 may be used with the transducer 70.

Again as similarly described above with reference to FIG. 4, a magnet 28 may produce a magnetic field generally perpendicular to coils segments of each coil 72. The coils 72 and/or the insulator 74 may be generally planar or non-planar.

The transducer 70 may be configured as an electromagnetic shockwave bi-polar transducer wherein the current source 76 sequentially delivers to the respective coils 72 current pulses of same polarity and/or of opposite polarity so as to produce sequential pulses of pulling and/or pushing forces between the coils 72, so as to produce and transmit sequential pulses of rarefaction and compression acoustic waves (to the acoustic conductive interface).

What is claimed is:

1. An electromagnetic shockwave transducer comprising: a double-faced coil of wire wound around an insulator, said coil having a first coil face on one side of said insulator and a second coil face on an opposite side of said insulator, wherein coil ends of said coil are electrically coupled to a current source, which produces a current pulse in said coil so as to produce a force between said coil faces, and wherein said insulator comprises a planar sheet having first and second planar surfaces and first and second edges at opposite ends of said first and second planar surfaces, and wherein one portion of said wire lies across said first planar surface, wraps around said first edge and then lies across said second planar surface, and then wraps around said second edge and then again lies across said first planar surface at a distance apart from where it previously lied across said first planar surface, and then again wraps around said first edge and then again lies across said second planar surface at a distance apart from where it previously lied across said second planar surface, and then again wraps around said second edge and then again lies across said first planar surface at a distance apart from where it previously lied across said first planar surface.

2. The electromagnetic shockwave transducer according to claim 1, further comprising an acoustically conductive interface, adjacent one or both of said coil faces, and through which said force produces an acoustic wave.

3. The electromagnetic shockwave transducer according to claim 2, wherein said acoustically conductive interface is attached to one or both of said coil faces.

4. The electromagnetic shockwave transducer according to claim 1, wherein current in said first coil face flows in an opposite direction to current in said second coil face.

5. The electromagnetic shockwave transducer according to claim 1, wherein each of said coil faces comprises generally parallel coil segments.

6. The electromagnetic shockwave transducer according to claim 1, wherein said double-faced coil comprises two or more serially-connected sub-coils.

7. The electromagnetic shockwave transducer according to claim 1, further comprising a magnet configured to produce a magnetic field generally perpendicular to coil segments of each said coil face.

8. The electromagnetic shockwave transducer according to claim 1, wherein said coil faces and/or said insulator are generally planar.

9. The electromagnetic shockwave transducer according to claim 1, wherein said coil faces and/or said insulator are generally non-planar.

10. The electromagnetic shockwave transducer according to claim 1, further comprising an acoustic lens and/or an acoustic reflector.

11. The electromagnetic shockwave transducer according to claim 1, wherein said insulator is a planar insulator.

12. The electromagnetic shockwave transducer according to claim 1, wherein said insulator comprises insulation of said wire.

13. A shockwave transducer comprising:
two similarly shaped and parallel flat coils of wire separated by a restoring insulator, said coils being in electrical communication with a current source, wherein said current source has an operative configuration to deliver current pulses of same polarity to said coils so as to produce pulses of pulling forces that pull said coils towards each other, said pulling forces producing rarefaction shockwaves, and
wherein said insulator comprises a planar sheet having first and second planar surfaces and first and second edges at opposite ends of said first and second planar surfaces, and wherein one portion of said wire lies across said first planar surface, wraps around said first edge and then lies across said second planar surface, and then wraps around said second edge and then again lies across said first planar surface at a distance apart from where it previously lied across said first planar surface, and then again wraps around said first edge and then again lies across said second planar surface at a distance apart from where it previously lied across said second planar surface, and then again wraps around said second edge and then again lies across said first planar surface at a distance apart from where it previously lied across said first planar surface.

14. A method of producing rarefaction shockwaves comprising:
providing an electromagnetic rarefaction shockwave transducer that comprises two similarly shaped and parallel flat coils of wire separated by a restoring insulator, said coils being in electrical communication with a current source, and using said current source to deliver current pulses of same polarity to said coils so as to produce pulses of pulling forces that pull said coils towards each other, said pulling forces producing rarefaction shockwaves, and wherein said insulator comprises a planar sheet having first and second planar surfaces and first and second edges at opposite ends of said first and second planar surfaces, and wherein one portion of said wire lies across said first planar surface, wraps around said first edge and then lies across said second planar surface, and then wraps around said second edge and then again lies across said first planar surface at a distance apart from where it previously lied across said first planar surface, and then again wraps around said first edge and then again lies across said second planar surface at a distance apart from where it previously lied across said second planar surface, and then again wraps around said second edge and then again lies across said first planar surface at a distance apart from where it previously lied across said first planar surface.

* * * * *